United States Patent [19]

Fabinski et al.

[11] Patent Number: 4,671,664

[45] Date of Patent: Jun. 9, 1987

[54] PHOTOMETER FOR MEASURING HOT GASES

[75] Inventors: Walter Fabinski, Kriftel; Willi Apel, Frankfurt; Guenter Bernhardt, Frankfurt; Rudolf Jezdinsky, Frankfurt; Heinz Wolf, Kronberg, all of Fed. Rep. of Germany

[73] Assignee: Hartmann & Braun AG, Frankfurt am Main, Fed. Rep. of Germany

[21] Appl. No.: 772,771

[22] Filed: Sep. 5, 1985

[30] Foreign Application Priority Data

Sep. 7, 1984 [DE] Fed. Rep. of Germany ....... 3432874

[51] Int. Cl.⁴ .............................................. G01N 21/01
[52] U.S. Cl. .................................... 356/440; 356/437; 250/573
[58] Field of Search ................ 356/213, 216, 220, 437, 356/438, 439, 440; 250/573, 574, 343, 576

[56] References Cited

U.S. PATENT DOCUMENTS 3,833,305  9/1974  Porter et al. ...................... 356/438
4,251,727  2/1981  Piercy ............................. 356/440 X

FOREIGN PATENT DOCUMENTS 1136064  1/1985  U.S.S.R. ........................... 356/438

Primary Examiner—Eugene R. Laroche
Assistant Examiner—Robert J. Pascal
Attorney, Agent, or Firm—Ralf H. Siegemund

[57] ABSTRACT

A photometer includes a radiation source, a measuring chamber and a receiver, all arranged in a casing and through coupling-decoupling members definite temperature gradients are produced between the measuring chamber and the receiver-transmitter and other gradients through appropriate coupling members are established towards the cooled housing.

11 Claims, 3 Drawing Figures

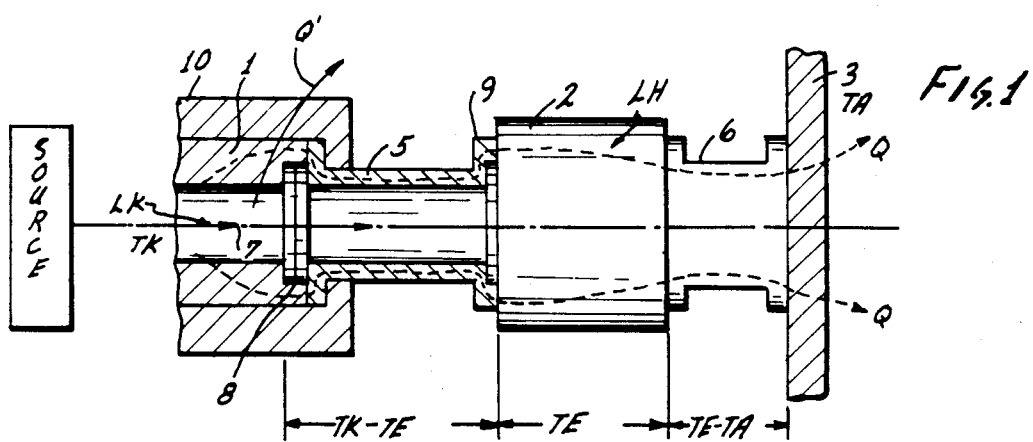
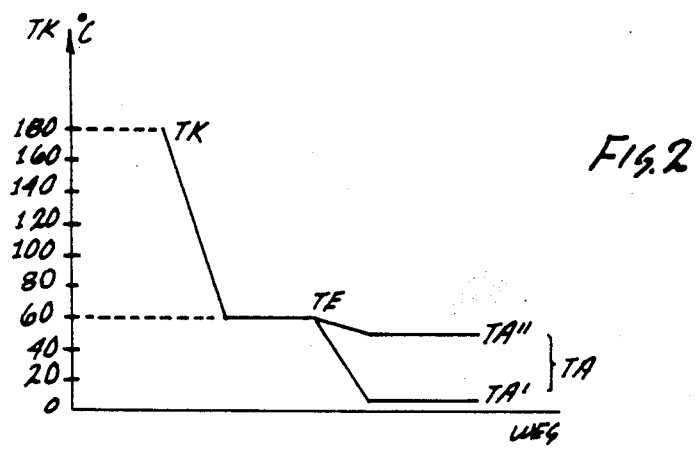
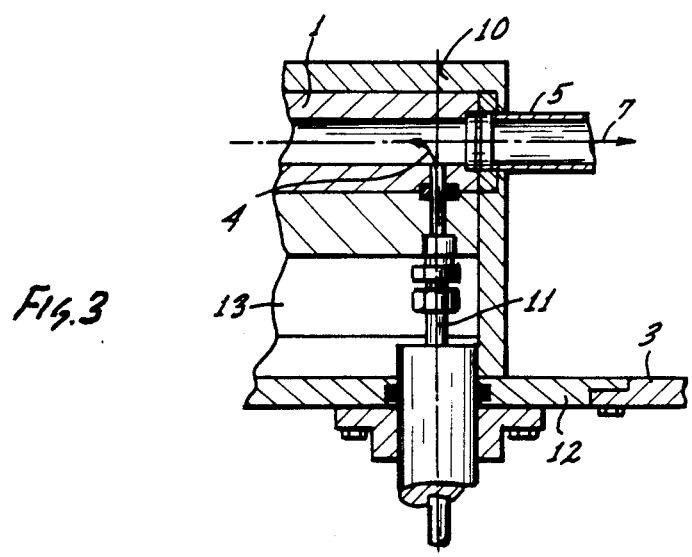

PHOTOMETER FOR MEASURING HOT GASES

BACKGROUND OF THE INVENTION

The present invention relates to a photometer designed for measuring a radiation which has passed through for example a stream of hot gases. More particularly the invention relates to a photometer in which for example in a single housing is provided a source of radiation, a cuvette or chamber with charge and discharge paths for the hot gas as well as a radiation receiver set whereby particularly the gas is expected to be at elevated temperatures.

In photometers of the type to which the invention pertains one has observed a number of problems which can also be termed thermic or thermo problems because they arise on account of the elevated temperature of the measuring object, namely, a hot gas. This hot gas flows through the measuring chamber whereby for example condensation occurs of any water vapor that may be contained in the gas. This phenomenon can particularly be observed if the measuring chamber itself has a temperature below a particular value, (e.g. the dew point). Thus, care has to be taken that the temperature of the measuring chamber will remain in a particular range for example at about one hundred eighty (180) degrees C. with a tolerance of plus or minus five (5) degrees C. Alternatively it may be advisable to consider this temperature of one hundred eighty (180) degrees a minimum temperature and to prevent merely through control action the dropping of the temperature of the chamber below one hundred eighty (180) degrees.

It is now well known that the stability of a receiver in a conventional photometer is not certain and cannot be expected to be maintained if there are considerable temperature variations to which the receiver is exposed. This in effect can be observed in all kinds of receivers which have been used in photometers. In the case for example of an opto pneumatic receiver temperature variations interfere with the formation of absorption lines which then indirectly induces a temperature dependent error in the measuring results while on the other hand the sensitivity of the equipment deteriorates.

Another effect of temperature variations is to be seen in that they reduce the use-life of the receiver possibly also of the radiation source particularly because the mounting facility for theses pieces of equipment as well as any modulation structure that may be included are in fact excessively subjected to high temperatures.

DESCRIPTION OF THE INVENTION

It is an object of the present invention to provide a new and improved photometer for measuring absorption in hot gases such that temperature variations particularly of the gas can be suppressed and high temperatures can be kept away from critically temperature sensitive parts of the photometer such as the radiation source and the receiver.

In accordance with the preferred embodiment of the present invention it is suggested to mount the radiation source, the measuring chamber including its charge or feed and discharge paths, and the receiver within a casing which is thermally conductive, and to provide thermal coupling by means of poorly heat conducting members, for the production of well defined heat flows as they emerge from the hot measuring chamber to lead to other parts of the photometer which coupling members moreover connect the radiation source and the receiver on one hand with the measuring chamber as well as the casing on the other hand so as to establish well defined temperature gradients from measuring chamber to the receiver and to the source and from there to the housing which as stated is thermally conductive so that heat can be dissipated from there. The invention therefore makes sure that the housing or casing is included in a well defined manner in the temperature distribution and heat flow of the photometer as a whole. The basic aspect is to provide a continuous on steady state heat flow from so to speak the prime source of thermal energy namely the hot measuring chamber towards the casing or housing which for purposes of dissipating the thermal energy into the environment may be provided with cooling elements, ribs, heat conductive sheets, vanes etc. From a thermal point of view, the radiation source and receiver are inserted in suitable points in that heat flow path so that under steady state conditions these elements assume the appropriate equilibrium temperature.

It was found to be of advantage to make the coupling members of a high grade steel for example in accordance with DIN 14571. Also another poorly heat conductive material such as polyimid can be used. The particular thermal coupling members which have to guide also the light rays such as the coupling member connecting radiation source and measuring chamber or the coupling member between measuring chamber and receiver should be constructed in the form of a hollow cylinder being gold plated on the inside. The highly reflective inside of that hollow cylinder supports significantly the conduction of radiation. The hollow configuration of coupling members permits their use as filtering chambers. Finally it should be mentioned that the temperature of the various critical elements, i.e. the temperature of the measuring chamber and of the receiver and of course also of the radiation source may be monitored and controlled by means of thermostats which means that if the temperature of any of these elements drops, heat is supplied thereto in order to restore the steady state conditions outlined above.

DESCRIPTION OF THE DRAWINGS

While the specification concludes with claims, particularly pointing out and distinctly claiming the subject matter which is regarded as the invention, it is believed that the invention, the objects and features of the invention, and further objects, features and advantages thereof, will be better understood from the following description taken in connection with the accompanying drawings, in which:

FIG. 1 is a cross-section through a portion of the photometer constructed in accordance with the preferred embodiment of the present invention for practicing the best mode thereof;

FIG. 2 is a diagram in which temperature is ploted along a particular path of heat flow as it occurs in the device shown in FIG. 1; and FIG. 3 illustrates a supplemental detail of the device shown in FIG. 1 but on a smaller scale.

DESCRIPTION OF THE PREFERRED EMBODIMENT

Proceeding now to the detailed description of the drawing FIG. 1 illustrates a measuring chamber 1 having a radiation window 8, in fact only an end portion of chamber 1 is shown, the chamber extends further to the left of the drawing. Also shown is the radiation receiver 2 being disposed at a particular distance from the measuring chamber 1. The case or housing of the photometer is shown in parts only; the wall 3 pertains to that case or housing; its configuration is not important; it is, however, important that this case or housing encloses all of the equipment.

Hot gases to be analyzed flow in the direction of arrow 4 as particularly indicated in FIG. 3. In order to avoid condensation of water vapor that may be carried along by and in the hot gases which condensation moreover may occur on the inside wall of the measuring chamber 1 for example on the inside of the window 8, it is necessary to maintain the temperature of the measuring chamber 1 at a level not lower than one hundred eighty (180) degrees C. For reasons of stability the receiver 2 is adjusted or calibrated to obtain a measurement at a particular temperature of for example sixty (60) degrees C. The casing 3 on the other hand is exposed to environmental temperature which can be expected to be within the range from about five (5) degrees C. to about forty five (45) degrees C. This being the conditions generally the temperature distribution from the measuring chamber 1 to the housing wall 3 is shown in FIG. 2 and develops as follows.

In between the chamber 1 and the radiation receiver 2 there is provided a first hollow coupling member 5 constructed of heat impeding material and being dimensioned both in terms of geometry as well as with regard to the material employed such that the temperature is reduced from one hundred eighty (180) degrees to sixty (60) degrees C. In other words, of the coupling member 5 one end is heat conductively connected to the measuring chamber 1 having a temperature of one hundred eighty (180) degrees and the thermal conductive conditions thus establish a reduction in temperature down to sixty (60) degrees C. which is the temperature on which the receiver is assumed to operate. The interior wall of the tube 5 may be gold plated.

Analogously a coupling member 6 is connected between the receiver 2 and the casing 3. Member 6 is not necessarily of hollow construction but preferrably solid and conducting heat from the receiver 2 to the housing wall 3. Again the geometrical dimensions and physical properties of this member 6 are such that the temperature along that member 6 is reduced from the sixty (60) degrees C. of the receiver down to say ten (10) degrees C. Throughout the system the heat flow is as shown by the arrows and lines Q, and the temperature distribution as per FIG. 2 can be understood to be taken as far as the abscissa is concerned along that path.

As stated the coupling member 6 may be solid while coupling member 5 is a hollow cylinder because it has to be traversed by the radiation that leaves the chamber 1 through the window 8. There is analogously an entrance window 9 for the receiver 2, and the windows 8 and 9 may for example be infrared transparent in case the radiation utilized in this system is at least predominantly of the infrared variety.

The temperature of the measuring chamber can be adjusted as stated to have for example a vario of $TK=180$ degrees C. Let TE be the temperature of the receiver 2 and TA" and TA' should be the assumed limit values for the outer temperature, with $TA''>TA>TA'$, to which the casing 3 is exposed and which it is assumed to take up. The cascaded distribution of the temperature as per FIG. 2 is then characterized in the equipment as per FIG. 1 through the values TK, TK−TE, TE, TE−TA and TA. Generally speaking the coupling members 5 and 6 serve the function of in fact thermally decouple measuring chamber 1, receiver 2 and casing 3. This means that members 5 and 6 distribute the temperature drop TK−TA such that temperature TE occurs at the "joint" which so to speak is established by receiver 2, and the receiver will assume that temperature. If ambient temperature TA drops towards TA', receiver 2 may have to be heated to maintain its temperature TE. The temperatures of the measuring chamber 1 and of the receiver 2 (or the radiation source) are monitored through thermostats. In case the temperature drop is too large a particular amount of heat LK or LH may be added to the system in order to stabilize the overall temperature distribution. The situation may be quite analogous for the radiation source itself.

The situation however, may be somewhat more complex. Temperature difference generally between measuring chamber on one hand and either the receiver or the radiation source on the other hand amounts to about forty (40) to one hundred twenty (120) degrees C. The temperature difference between receiver and radiation source on one hand and casing 3 on the other hand is in the order of ten (10) to fifty (50) degrees C. These values occur simply on the basis of the particular temperatures the various components have or are suppose to have and to assume. Also as stated the external temperature may vary from five (5) to forty five (45) degrees C.

In order to avoid so called thermal bypasses it may be advisable to protect the measuring chamber 1 against the environmental air as far as temperature and heat flow is concerned. Generally this can be attained by using for example a mineral jacketing material 10 disposed to extend around the measuring chamber 1 and other parts. In order to avoid heat loss through radiation through parasitic radiation indicated for example by the arrow Q' the insulator 10 fulfills also that function. The gas conduits leading into and out of the measuring chamber 1 are analogously thermally insulated. It is advisable to avoid any interference of the thermal equilibrium for example via the conduits leading into and out of the measuring chamber. For this these conduits such as 11 are not only thermally insulated as already indicated but in addition they are mounted to the instrument by means of a special feed through structure 12 made of heat insulating material such as high grade steel.

The hollow member 5 coupling in the example the measuring chamber 1 to the receiver 2 or the analogously hollow constructed coupling member between the measuring chamber 1 and the radiation source can be used as a filtering chamber containing a particular gas which modifies in a particular manner the radiation for example as it leaves the measuring chamber 1 but before reaching the receiver 2.

It may be advisable to use different material for the coupling members 5 and 6 whereby particularly the heat conduction should differ by way of example the hollow coupling member 5 may be made of high grade steel and the coupling member 6 of aluminum. One or the other or both may be made of polyimid.

As shown in greater detail in FIG. 3 a heat conductive block 13 is mechanically and temperature conductively connected to the measuring chamber 1. This block 13 is provided as stated with elements for connecting the gas feed and discharge lines 11. This particular block may also be heated. The elements for receiving the gas and feed lines and discharge paths are independent from the length of the measuring chamber 1. The conductors running from the block 13 to the measuring chamber 1 however have a distance and spacing which is matched to the particular length of the measuring chamber.

In order to provide further control of the temperature distribution one may provide an angularly shaped cover for covering the elements provided to receive the feed and discharge lines.

The invention is not limited to the embodiments described above; but all changes and modifications thereof, not constituting departures from the spirit and scope of the invention, are intended to be included.

We claim:

1. In a photometer provided for measuring absorptive qualities of hot gases and being comprised of a case, a source of radiation, a receiver and a measuring chamber with feed and discharge lines, the improvement comprising:
   the case being made of a good temperture and heat conductor;
   a first thermal coupling member interposed between one of the radiation source and receiver, on one hand, and the measuring chamber on the other hand;
   a second thermal coupling member interposed between said one of the source and the receiver, and the casing, also in temperature conductive relationship such that a predetermined temperature gradient develops between the measuring chamber via the first coupling member to the receiver or radiation source and further via the second coupling member to the housing; and
   said coupling members conducting heat less efficiently than the case.

2. Photometer as in claim 1 wherein at least one of the first and second coupling members is made of high grade steel.

3. Photometer as in claim 1 wherein said coupling members are made of polyimide.

4. Photometer as in claim 1 wherein said first coupling member is made of a high grade steel and the second coupling member is made of aluminum.

5. Photometer as in claim 1 wherein said first coupling member is hollow and having a gold plated interior wall.

6. Photometer as in claim 1 wherein said measuring chamber is thermally isolated from the environment, by means of a jacket, being separated from the case.

7. Photometer as in claim 1 wherein the temperature of at least one of said measuring chamber, said radiation source and said receiver is controlled by a thermostat.

8. Photometer as in claim 1 wherein said feed and discharge lines are thermally insulated with reference to the housing.

9. Photometer as in claim 1 wherein the thermal resistance of the receiver or the radiation source is small as compared with the thermal resistance of the first and second coupling members.

10. Photometer as in claim 1 wherein said first coupling member is hollow and contains a filtering gas.

11. Photometer as in claim 1 including a heated, thermally conductive block being mechanically and thermally conductively connected to the measuring chamber, which block includes conduit elements for gas feeding and discharge.

* * * * *